United States Patent [19]

Scott et al.

[11] Patent Number: 4,902,848
[45] Date of Patent: Feb. 20, 1990

[54] PROCESS FOR THE DEHYDROGENATION OF HYDROCARBONS

[75] Inventors: Norman H. Scott, Arlington Heights; Bipin V. Vora, Darien, both of Ill.

[73] Assignee: UOP, Des Plaines, Ill.

[21] Appl. No.: 214,355

[22] Filed: Jul. 1, 1988

[51] Int. Cl.[4] .............................................. C07C 5/36
[52] U.S. Cl. ..................................... 585/655; 585/660
[58] Field of Search ........................ 585/654, 655, 660

[56] References Cited

U.S. PATENT DOCUMENTS

| | | | |
|---|---|---|---|
| 3,691,246 | 9/1972 | Parker et al. .................... | 585/655 X |
| 4,381,418 | 4/1983 | Gewartowski et al. ............ | 585/655 |
| 4,430,517 | 2/1984 | Imai et al. ............................ | 585/660 |
| 4,469,811 | 9/1984 | Lucien ................................. | 502/227 |
| 4,486,547 | 12/1984 | Imai et al. ............................ | 502/233 |

OTHER PUBLICATIONS

Vora, B. V., and Imai, T., "C$_2$/C$_5$ Dehydrogenation Updated", *Hydrocarbon Processing*, Apr. 1982, pp. 171–174.

*Primary Examiner*—Glenn Caldarola
*Attorney, Agent, or Firm*—Thomas K. McBride; John G. Tolomei; John G. Cutts, Jr.

[57] ABSTRACT

A process for the dehydrogenation of a dehydrogenatable hydrocarbon feedstock having small quantities of higher boiling range hydrocarbons which comprises: (a) introducing the dehydrogenatable hydrocarbon feedstock into a fractionation zone having at least a portion of reflux to a fractionation column supplied by the dehydrogenatable hydrocarbon feedstock to provide a dehydrogenatable hydrocarbon stream having a reduced concentration of higher boiling range hydrocarbons and a stream comprising the higher boiling range hydrocarbons; (b) introducing the dehydrogenatable hydrocarbon stream having a reduced concentration of higher boiling range hydrocarbon recovered in step (a) into a dehydrogenation zone containing dehydrogenation catalyst and operated at dehydrogenation conditions to provide a hydrocarbon stream comprising dehydrogenated hydrocarbons and unconverted dehydrogenatable hydrocarbons; (c) separating the hydrocarbon stream comprising dehydrogenated hydrocarbons and unconverted dehydrogenatable hydrocarbons from step (b) to provide a product stream comprising dehydrogenated hydrocarbons and a recycle stream comprising unconverted dehydrogenatable hydrocarbons; and (d) introducing the recycle stream comprising unconverted dehydrogenatable hydrocarbons recovered in step (c) into the fractionation column to provide at least a portion of feed to the fractionation column.

7 Claims, 1 Drawing Sheet

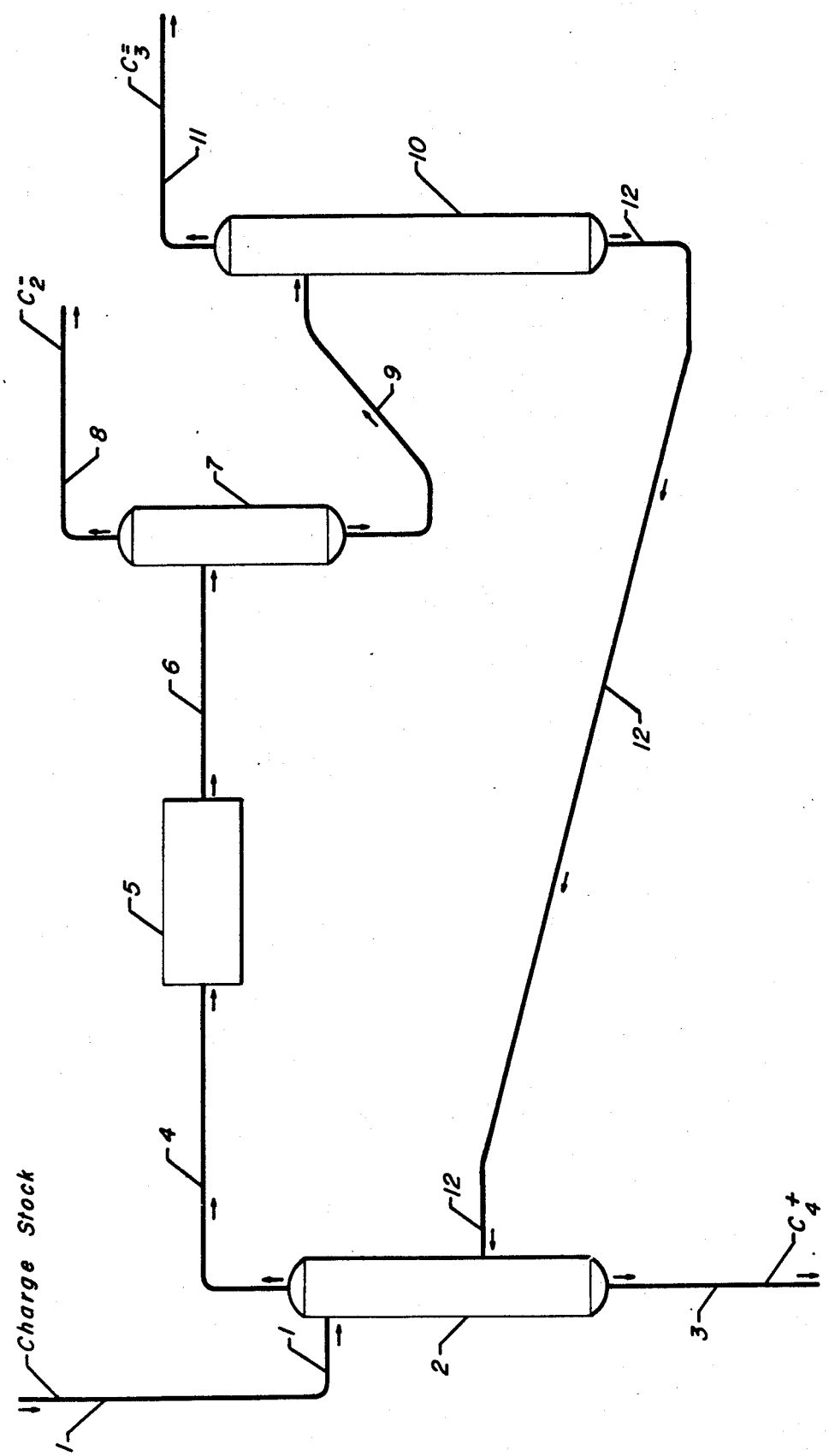

PROCESS FOR THE DEHYDROGENATION OF HYDROCARBONS

FIELD OF THE INVENTION

The present invention is directed toward an improved process for the dehydrogenation of dehydrogenatable hydrocarbons. More specifically, the invention relates to an integrated process wherein trace quantities of higher molecular weight compounds which are undesirable are removed from the dehydrogenatable hydrocarbon feedstock prior to the dehydrogenation step by means of utilizing the dehydrogenatable hydrocarbon feedstock as at least a portion of a reflux stream in the separation zone utilized to reject the undesirable higher molecular weight hydrocarbon compounds. Even more specifically, the invention relates to a process for the dehydrogenation of a dehydrogenatable hydrocarbon feedstock having small quantities of higher boiling range hydrocarbons which comprises: (a) introducing the dehydrogenatable hydrocarbon feedstock into a fractionation zone having at least a portion of reflux to a fractionation column supplied by the dehydrogenatable hydrocarbon feedstock to provide a dehydrogenatable hydrocarbon stream having a reduced concentration of higher boiling range hydrocarbons and a stream comprising the higher boiling range hydrocarbons; (b) introducing the dehydrogenatable hydrocarbon stream having a reduced concentration of higher boiling range hydrocarbon recovered in step (a) into a dehydrogenation zone containing dehydrogenation catalyst and operated at dehydrogenation conditions to provide a hydrocarbon stream comprising dehydrogenated hydrocarbons and unconverted dehydrogenatable hydrocarbons; (c) separating the hydrocarbon stream comprising dehydrogenated hydrocarbons and unconverted dehydrogenatable hydrocarbons from step (b) to provide a product stream comprising dehydrogenated hydrocarbons and a recycle stream comprising unconverted dehydrogenatable hydrocarbons; and (d) introducing the recycle stream comprising unconverted dehydrogenatable hydrocarbons recovered in step (c) into the fractionation column to provide at least a portion of feed to the fractionation column.

INFORMATION DISCLOSURE

Dehydrogenating hydrocarbons is an important commercial hydrocarbon conversion process because of the great demand for dehydrogenated hydrocarbons for the manufacture of various chemical products such as detergents, high octane motor fuels, pharmaceutical products, plastics, synthetic rubbers, polymerization monomers and other products well known to those skilled in the art. Processes for the dehydrogenation of light acyclic hydrocarbons are well known to those skilled in the hydrocarbon conversion arts. For instance, the dehydrogenation of $C_2$–$C_5$ paraffins is described in an article beginning at page 171 of the Apr. 1982 edition of *Hydrocarbon Processing*. Because the light paraffins are relatively volatile, a more complicated separation scheme and a bulk condensation is normally required to effect the separation of the product olefins from the light biproducts and hydrogen simultaneously produced in the process. It is therefore believed that U.S. Pat. No. 4,381,418 assigned to Gewartowski et al is pertinent for its teaching of a catalytic dehydrogenation process for $C_2+$ normally gaseous paraffinic hydrocarbons and the recovery of the products of the reaction. U.S. Pat. Nos. 4,430,517 and 4,486,547 issued to Imai et al and U.S. Pat. No. 4,469,811 issued to Lucien are believed pertinent for their teaching of catalysts and operating conditions which can be employed for the dehydrogenation of low molecular weight paraffins.

BRIEF SUMMARY OF THE INVENTION

The invention provides a process for the production of olefinic hydrocarbons which in certain instances will be highly advantageous in that trace quantities of undesirable high molecular weight hydrocarbons will be separated and rejected from the feedstock to provide a desirable stream of dehydrogenatable hydrocarbons. This integrated process achieves the demonstrated advantages by the use of the recycle stream comprising unconverted dehydrogenatable hydrocarbons as a feed in a separation zone used to reject the undesirable high molecular weight hydrocarbons while simultaneously purifying the recycle stream. The feedstock of the process is introduced into the separation zone used to reject the undesirable high molecular weight hydrocarbons as at least a portion of the reflux.

One broad embodiment of the present invention may be characterized as a process for the dehydrogenation of a dehydrogenatable hydrocarbon feedstock having small quantities of higher boiling range hydrocarbons which comprises: (a) introducing the dehydrogenatable hydrocarbon feedstock into a fractionation zone having at least a portion of reflux to a fractionation column supplied by the dehydrogenatable hydrocarbon feedstock to provide a dehydrogenatable hydrocarbon stream having a reduced concentration of higher boiling range hydrocarbons and a stream comprising the higher boiling range hydrocarbons; (b) introducing the dehydrogenatable hydrocarbon stream having a reduced concentration of higher boiling range hydrocarbon recovered in step (a) into a dehydrogenation zone containing dehydrogenation catalyst and operated at dehydrogenation conditions to provide a hydrocarbon stream comprising dehydrogenated hydrocarbons and unconverted dehydrogenatable hydrocarbons; (c) separating the hydrocarbon stream comprising dehydrogenated hydrocarbons and unconverted dehydrogenatable hydrocarbons from step (b) to provide a product stream comprising dehydrogenated hydrocarbons and a recycle stream comprising unconverted dehydrogenatable hydrocarbons; and (d) introducing the recycle stream comprising unconverted dehydrogenatable hydrocarbons recovered in step (c) into the fractionation column to provide at least a portion of feed to the fractionation column.

Other embodiments of the subject invention encompass further details such as preferred feedstocks, dehydrogenation catalysts and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

Olefinic hydrocarbons are one of the major building blocks of a large number of petrochemical products. Olefinic hydrocarbons are also useful in petroleum refineries for the production of motor fuel blending components. The process of the present invention possesses utility in providing facile production of these olefinic hydrocarbons. As a practical matter even highly purified dehydrogenatable hydrocarbon charge stocks contain at least trace quantities of hydrocarbons which possess a molecular weight greater than the desired dehydrogenatable hydrocarbon charge stock. In the event that these higher molecular weight hydrocarbons are introduced into the dehydrogenation zone, they are subsequently recycled and thereby their concentration tends to build up in the recycle stream. The higher molecular weight hydrocarbons are then only rejected by cracking in the dehydrogenation zone to form lower molecular weight hydrocarbons which are subsequently removed from the overall dehydrogenation process. The cracking of high molecular weight hydrocarbons in the dehydrogenation zone causes coking on the dehydrogenation catalyst which tends to shorten the ultimate life of the catalyst and is therefore an undesirable feature of the prior art processes. It is preferred that the high molecular weight hydrocarbons have a concentration of less than about 10 wt. percent and more preferably less than about 5 wt. percent based on the dehydrogenatable hydrocarbon feedstock. We have discovered an integrated dehydrogenation process which overcomes these disadvantages and the details of which process are herein described.

Propylene has become a very valuable monomer due to increasing demand for polypropylene. Propylene may be produced by dehydrogenating propane, which is recovered in abundance from natural gas fields. A typical propane feed will consist of 1–2% light components such as, for example, ethane and 2–10% heavy components such as, for example, butane. These light hydrocarbon components do not pose any significant problem during processing, except for the fact that they occupy space, because they can be rejected in a separation zone of the dehydrogenation process.

Heavy hydrocarbon components can be removed by prefractionation of the feed. In theory at least, it is possible to remove all of the heavy hydrocarbon components (butane) as a bottoms product from the fractionation column and obtain clean overhead propane product which is free of heavies and which may be used as a feed for dehydrogenation. However, this course of action will require an expensive fractionation column with many trays and will require a high volume of fractionation column reflux. In practice, however, it is typical to obtain overhead propane product from a depropanizer fractionation column containing 1–3% butane which permits the use of a reasonably economical fractionation column design.

Since the dehydrogenation is an equilibrium limited reaction, the dehydrogenation product, after light ends removal, comprises the feed paraffin (for example, propane), product olefins (for example, propylene), as well as minor amounts of butanes and butenes. In order to maximize the production of propylene, it is desirable to recycle the unconverted feed paraffin (propane), after separation of olefin product (propylene), to the dehydrogenation zone for its complete conversion to olefin product (propylene). This recycle of feed paraffin, depending upon feed butane concentration, comprises butane and butenes, as well as minor amounts of di-olefins.

The hereinbelow presented data show normal boiling points and relative fractionation coefficients of $C_3$–$C_4$ hydrocarbons.

| Component | Normal Boiling Point, °C. | Fractionation Coefficient @ 38° C., 1 ATM |
|---|---|---|
| Propylene | −53.28 | 2.48 |
| Propane | −42.06 | 2.15 |
| Propadiene | −34.50 | 1.73 |
| Methylacetylene | −23.22 | 1.54 |
| Isobutane | −11.73 | 1.00 |
| Isobutene | − 6.90 | 0.89 |
| n-Butene-1 | − 6.26 | 0.87 |
| 1,3 Butadiene | − 4.41 | 0.84 |
| n-Butane | − 0.50 | 0.74 |
| t-2, n butene | + 0.88 | 0.70 |
| c-2, n butene | + 3.72 | 0.68 |

The hereinabove presented data show that $C_4$-olefins are higher boiling components than isobutane. Thus, the returning of recycle stream to the feed fractionation column makes the task of $C_4$ rejection significantly easier. The return of the recycle stream to the feed fractionation column also avoids the buildup of $C_4$ olefins and di-olefins in the recycle stream and which buildup would otherwise result in increased coke formation and the acceleration of the deactivation of the dehydrogenation catalyst. The introduction of the feedstock as at least a portion of the reflux of the feed fractionation column minimizes utilities and the expense therefor.

The term "dehydrogenatable hydrocarbons" as utilized herein is meant to refer to all classes of hydrocarbons containing saturated carbon bonds which have the potential for forming one or more unsaturated bonds through the process of dehydrogenation. The preferred dehydrogenatable hydrocarbons of the present invention consist of paraffinic type hydrocarbons. More specifically, the paraffin hydrocarbon charge stock of the present invention may contain from 2 carbon atoms to about 30 carbon atoms. Representative members of this class are: ethane, propane, butane, pentane, hexane, heptane, nonane, decane, undecane, dodecane, tridecane, tetradecane, pentadecane, hexadecane, heptadecane, octadecane, and mixtures thereof. A particularly important class of charge stocks include ethane, propane, butane, pentane and mixtures thereof and which are readily prepared by the fractionation of relatively low boiling point hydrocarbon fractions. Another important charge stock contains normal paraffins of about 10 to about 15 carbon atoms since these produce a mono-olefin which can be utilized to make detergents having superior biodegradability and detergency. For example, a mixture containing a 4 or 5 homolog spread, such as $C_{11}$ to $C_{14}$, $C_{10}$ to $C_{13}$, $C_{11}$ to $C_{15}$, provides an excellent charge stock. Moreover, it is preferred that the amount of nonnormal hydrocarbons present in this normal paraffin stream be kept at low levels. Thus, it is preferred that this stream contain greater than 90 wt. % normal paraffin hydrocarbons, with best results achieved at purities in the range of 96–99 wt. % or more. Typically, the feed dehydrogenatable hydrocarbons to a catalytic dehydrogenation process contains admixed therewith contaminants typically comprising hydrogen, light hydrocarbons having less carbon atoms per molecule than the desired feed hydrogenatable hydrocarbon and heavy hydrocarbons having more carbon atoms per molecule than the desired feed dehydrogenatable hydrocarbon. One of the primary advantages of the present invention is the ability to easily and economically remove trace quantities of hydrocarbon contaminants having more carbon atoms per molecule than the desired feed dehydrogenatable hydrocarbon.

Although various types of hydrocarbon feedstocks may be utilized in the process of the present invention, for purposes of specific exemplification, a feed stream comprising a high percentage of propane with trace quantities of butane is described in detail.

In accordance with the present invention, the dehydrogenatable hydrocarbon charge stock is introduced as at least a portion of the reflux into a fractionation zone which comprises a fractionation column. At least a portion of the feed to the fractionation column is supplied by a hereinafter described recycle stream. The use of the feedstock to reflux the fractionation column provides several advantages including the minimization of utilities, the prevention of buildup of high molecular weight hydrocarbons which boil at a temperature greater than the desired olefinic product, the enhancement of the dehydrogenation catalyst life, and the rejection of high molecular weight hydrocarbon compounds which are associated with the dehydrogenatable hydrocarbon charge stock. The separation zone utilized in the present invention may employ any convenient and known separation techniques and preferably comprises a fractionation column. The design and operation of the contemplated and preferred fractionation column are well known to those skilled in the art. However, in accordance with the present invention, it is essential that at least a portion of the reflux utilized in the fractionation column be comprised of the feedstock.

In order to enjoy the maximum benefits of the present invention, it is preferable to adjust the temperature of the reflux stream to the fractionation column by means of indirect heat exchange. The preferred fractionation column is operated to provide a dehydrogenatable hydrocarbon stream having a reduced concentration of higher boiling range hydrocarbons and a stream comprising the higher boiling range hydrocarbons. The resulting dehydrogenatable hydrocarbon stream having a reduced concentration of higher boiling range hydrocarbons is introduced into a dehydrogenation zone containing dehydrogenation catalyst and operated at dehydrogenation conditions to convert at least a portion of the dehydrogenatable hydrocarbons to provide a hydrocarbon stream comprising dehydrogenated hydrocarbons and unconverted dehydrogenatable hydrocarbons.

The dehydrogenation catalyst may be employed in a fixed bed, fluidized bed, or a moving bed. Moreover, the dehydrogenation catalytic reaction zone may consist of multiple catalyst beds. In one such system, the catalyst is employed within an annular bed through which it is movable via gravity flow. In such a system, it is common practice to remove catalyst from the bottom of the reaction zone, regenerate it and then return it to the top of the reaction zone. Any suitable dehydrogenation catalyst may be used in the process of the present invention. Generally, the preferred catalyst comprises a platinum group metal component, an alkali metal component and a porous inorganic carrier material. The catalyst may also contain promoter metals which advantageously improve the performance of the catalyst. It is preferable that the porous carrier material of the dehydrogenation catalyst be an absorptive high surface area support having a surface area of about 25 to about 500 m$^2$/g. The porous carrier material should be relatively refractory to the conditions utilized in the reaction zone and may be chosen from those carrier materials which have traditionally been utilized in dual function hydrocarbon conversion catalysts. A porous carrier material may therefore be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxide such as alumina, titanium dioxide, zirconium dioxides, magnesia, silica alumina, alumina boria; crystalline alumina silicates such as naturally occurring or synthetically prepared mordenite or a combination of one or more of these materials. The preferred porous carrier material is a refractory inorganic oxide, with the best results being obtained with an alumina carrier material. The aluminas, such as gamma alumina, give the best results in general. The preferred catalyst will have a gamma alumina carrier which is in the form of spherical particles having relatively small diameters on the order of about 1/16".

The preferred dehydrogenation catalyst also contains a platinum group metal component. Of the platinum group metals, which include palladium, rhodium, ruthenium, osmium or iridium, the use of platinum is preferred. The platinum group component may exist within the final catalyst composite as a compound such as an oxide, sulfide, halide, oxysulfide, etc., of an elemental metal or in combination with one or more other ingredients of the catalyst. It is believed that the best results are obtained when substantially all the platinum group components exist in the elemental state. The platinum group component generally comprises from about 0.01 to about 2 wt. % of the final catalytic composite, calculated on an elemental basis. It is preferred that the platinum content of the catalyst be between about 0.2 and 1 wt. %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material.

Additionally, the preferred catalyst contains an alkali metal component chosen from cesium, rubidium, potassium, sodium, and lithium. The preferred alkali metal is normally either potassium or lithium, depending on the feed hydrocarbon. The concentration of the alkali metal may range from about 0.1 to 3.5 wt. %, but is preferably between 0.2 and about 2.5 wt. % calculated on an elemental basis. This component may be added to the catalyst by the methods described above as a separate step or simultaneously with the solution of another component.

As noted previously, the dehydrogenation catalyst may also contain promoter metal. One such preferred promoter metal is tin. The tin component should constitute about 0.01 to about 1 wt. % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. Thus, the component may be added to the carrier by coprecipitation.

A preferred method of incorporating the tin component involves coprecipitation during the preparation of the preferred carrier material. This method typically involves the addition of a suitable soluble tin compound, such as stannous or stannic chloride to an alumina hydrosol, mixing these ingredients to obtain a uniform distribution throughout the sol and then combining the hydrosol with a suitable gelling agent and dropping the resultant admixture into an oil bath. The tin component may also be added through the utilization of a soluble decomposable compound of tin to impregnate the calcined porous carrier material. A more detailed description of the preparation of the carrier material and the addition of the platinum component and the tin component to the carrier material may be obtained by reference to U.S. Pat. No. 3,745,112.

The dehydrogenation conditions which will be employed in the process of the present invention will of course vary depending on such factors as catalyst activity, feedstock, and desired conversion. A general range of conditions which may be employed for dehydrogenation of a light hydrocarbon include a temperature of from about 1022° F. (550° C.) to about 1472° F. (800°)C., a pressure of from about 0.01 to about 10 atmospheres absolute, a liquid hourly space velocity between about 0.1 and about 100 hr$^{-1}$ and a hydrogen to hydrocarbon mole ratio from about 0.01:1 to about 40:1.

In accordance with the present invention, a hydrocarbon stream, for example, comprising propylene, propane, ethylene, ethane, methane, and trace quantities of hydrogen, butane and butylene, is removed from the dehydrogenation reaction zone and is subjected to separation in order to recover a product stream comprising propylene. This separation may be conducted in a separation zone using conventional gas/liquid separation, fractionation columns and techniques which are well known to those skilled in the art. It is preferable that the hydrocarbon stream, as described hereinabove, for example, be introduced after removal of most of the hydrogen into a de-ethanizer column in order to provide an overhead stream comprising ethylene, ethane, methane and hydrogen and to provide a bottom stream which is introduced into a propylene column. The propylene column is preferably operated to provide an overhead product stream comprising propylene and a bottoms stream comprising unconverted propane and minor quantities of butane and butylene. This resulting bottoms stream comprising predominantly unconverted propane is referred to as a recycle stream which will eventually be returned to the dehydrogenation reaction zone and which is utilized to provide at least a portion of the feed to the fractionation column as previously described. The design, construction and operation of the various components to accomplish the separation of the dehydrogenation reaction zone effluent are well known to the skilled artisan and need not be reiterated here for a full and complete understanding of the present invention even in the event that a feedstock other than propane is selected for dehydrogenation.

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

With reference now to the drawing, a dehydrogenatable hydrocarbon feed stream comprising propane and trace quantities of butane is introduced via conduit 1 into fractionator 2 as at least a portion of the reflux required for fractionator 2. A recycle stream is introduced via conduit 12 as feed to fractionator 2 and which is prepared as hereinafter described. A purified stream of dehydrogenatable hydrocarbon comprising propane is removed from fractionator 2 via conduit 4 and introduced into dehydrogenation zone 5 to dehydrogenate at least a portion of the propane stream to provide dehydrogenated hydrocarbons. A hydrocarbon stream comprising dehydrogenated hydrocarbons and unconverted dehydrogenatable hydrocarbons is removed from dehydrogenation zone 5 via conduit 6 and introduced into separation zone 7. Separation zone 7 is operated as a deethanizer and an overhead stream comprising predominantly hydrogen, ethane and lighter hydrocarbons is removed via conduit 8 and recovered. A hydrocarbon stream comprising predominantly $C_3$ and heavier hydrocarbons is removed from separation zone 7 via conduit 9 and introduced into separation zone 10. A hydrocarbon stream rich in dehydrogenated hydrocarbon is removed from separation zone 10 via conduit 11 and recovered as a primary product stream. A hydrocarbon stream comprising dehydrogenatable hydrocarbon, in this case, propane, and any other higher molecular weight hydrocarbons which may be present is removed from separation zone 10 via conduit 12 which serves as at least a portion of the feed to fractionator 2 as hereinabove described.

The process of the present invention is further demonstrated by the following illustrative embodiment. This illustrative embodiment is, however, not presented to unduly limit the process of this invention, but to further illustrate the advantages of the hereinabove described embodiments. The following data were not obtained by the actual performance of the present invention, but are considered prospective and reasonably illustrative of the expected performance of the invention.

ILLUSTRATIVE EMBODIMENT

A typical propane feed for a propane dehydrogenation process contains from about 0.5 to about 5 weight percent butane. In prior art dehydrogenation processes, the introduction of such a propane feed results in a buildup of butane in the propane recycle stream to the dehydrogenation catalyst and thereby increases the volume of the combined feed to the catalyst. The presence of butane occupies space and requires heating during the processing of propane and does not contribute to the desired product. Another disadvantage of the presence and circulation of butane is that during each pass through the reactor a small portion of the butane is converted to coke on the surface of the catalyst which tends to eventually shorten the life of the catalyst. A summary of a prior art propane dehydrogenation process which has no rejection of butane is presented in Table 1.

TABLE 1

SUMMARY OF OPERATION - NO REJECTION OF BUTANE

Feed: 95 wt. % $C_3$, 1 wt. % $C_2$, 4 wt. % $C_4$
Units: Mass Units Per Hour

| Stream No. | 1 | 2 | 3 | 4 | 5 | 6 |
|---|---|---|---|---|---|---|
| Stream Description | $C_3$ Feed | Recycle | Reactor Combined Feed | Net Gas | Propylene Product | $C_4$ Rejection |
| $H_2$ | | | | 406 | | |
| $C_1$ | | | | 596 | | |
| $C_2$ | 121 | | 121 | 1003 | 1 | |
| $C_3=$ | | 208 | 208 | 38 | 9947 | |
| $C_3$ | 11456 | 17444 | 28900 | 17 | 50 | |
| Pd + MeAC | — | 5 | 5 | | | |
| $C_4$ | 483 | 2340 | 2823 | | 2 | |
| $C_4=$ | | 2056 | 2056 | | | |
| Total | 12060 | 22053 | 34113 | 2060 | 10000 | None |

In accordance with the present invention, a propane dehydrogenation process which incorporates the rejection of butane is summarized and presented in Table 2.

TABLE 2

SUMMARY OF OPERATION - WITH REJECTION OF BUTANE

Feed: 95 wt. % $C_3$, 1 wt. % $C_2$, 4 wt. % $C_4$
Units: Mass Units Per Hour

| Stream No. | 1 | 2 | 3 | 4 | 5 | 6 |
|---|---|---|---|---|---|---|
| Stream Description | $C_3$ Feed | Recycle | Reactor Combined Feed | Net Gas | Propylene Product | $C_4$ Rejection |
| $H_2$ | | | | 429 | | |
| $C_1$ | | | | 471 | | |
| $C_2$ | 125 | | 125 | 1005 | 1 | |
| $C_3=$ | | 208 | 208 | 38 | 9950 | |
| $C_3$ | 11885 | 17344 | 29229 | | 49 | 105 |
| Pd+MeAC | — | 5 | 5 | | | 205 |
| $C_4$ | 500 | 137 | 637 | | | 240 |
| $C_4=$ | | 60 | 60 | | | |
| Total | 12510 | 17754 | 30264 | 1960 | 10000 | 550 |

From the hereinabove presented tables, it is to be noted that for the same propane product of 10,000 mass units/hr. in each case, the combined feed to the dehydrogenation reaction zone in the process of the present invention is only 88.7% (30264/34113) of that to the prior art process which translates into the savings resulting from the requirement to build a dehydrogenation reaction zone which is nearly 13% smaller in size. In addition, the utilities required to heat the larger volume of combined feed and further fractionate the reaction effluent is also saved.

The foregoing description, drawing and illustrative embodiment clearly illustrate the advantages encompassed by the process of the present invention and the benefits to be afforded with the use thereof.

We claim:

1. A process for the dehydrogenation of a dehydrogenatable hydrocarbon feedstock having small quantities of higher boiling range hydrocarbons which comprises:
   (a) introducing said dehydrogenatable hydrocarbon feedstock into a fractionation zone having at least a portion of reflux to a fractionation column supplied by said dehydrogenatable hydrocarbon feedstock to provide a dehydrogenatable hydrocarbon stream having a reduced concentration of higher boiling range hydrocarbons and a stream comprising said higher boiling range hydrocarbons;
   (b) introducing said dehydrogenatable hydrocarbon stream having a reduced concentration of higher boiling range hydrocarbon recovered in step (a) into a dehydrogenation zone containing dehydrogenation catalyst and operated at dehydrogenation conditions to provide a hydrocarbon stream comprising dehydrogenated hydrocarbons and unconverted dehydrogenatable hydrocarbons;
   (c) separating said hydrocarbon stream comprising dehydrogenated hydrocarbons and unconverted dehydrogenatable hydrocarbons from step (b) to provide a product stream comprising dehydrogenated hydrocarbons and a recycle stream comprising unconverted dehydrogenatable hydrocarbons; and
   (d) introducing said recycle stream comprising unconverted dehydrogenatable hydrocarbons recovered in step (c) into said fractionation column to provide at least a portion of feed to said fractionation column.

2. The process of claim 1 wherein said dehydrogenatable hydrocarbon feedstock is selected from the group consisting of ethane, propane, butane, and pentane.

3. The process of claim 1 wherein said higher boiling range hydrocarbons are present in said dehydrogenatable hydrocarbon feedstock in an amount less than about 10 weight percent.

4. The process of claim 1 wherein said dehydrogenation conditions include a temperature from about 1022° F. (550° C.) to about 1472° F. (800° C.), a pressure from about 0.01 to about 10 atmospheres absolute, a liquid hourly space velocity from about 0.1 to about 100 $hr^{-1}$ and a hydrogen to hydrocarbon mole ratio from about 0.01:1 to about 40:1.

5. The process of claim 1 wherein said dehydrogenation catalyst comprises a platinum group metal component, an alkali metal component and a porous inorganic carrier material.

6. The process of claim 1 wherein said step (c) is conducted in a separation zone comprising a deethanizer fractionation column and a propylene fractionation column.

7. The process of claim 1 wherein said dehydrogenatable hydrocarbon feedstock comprises propane and small quantities of butane.

* * * * *